United States Patent

Ishiyama et al.

[11] Patent Number: 6,063,587
[45] Date of Patent: May 16, 2000

[54] WATER-SOLUBLE TETRAZOLIUM SALT COMPOUNDS

[75] Inventors: Munetaka Ishiyama; Yoko Miyazono; Masanobu Shiga; Kazumi Sasamoto, all of Kumamoto, Japan

[73] Assignee: Dojindo Laboratories Co., Ltd., Kumamoto, Japan

[21] Appl. No.: 09/147,139

[22] PCT Filed: Apr. 17, 1997

[86] PCT No.: PCT/JP97/01324

§ 371 Date: Dec. 8, 1998

§ 102(e) Date: Dec. 8, 1998

[87] PCT Pub. No.: WO97/38985

PCT Pub. Date: Oct. 23, 1997

[30] Foreign Application Priority Data

Apr. 18, 1996 [JP] Japan ................................ 8-121134

[51] Int. Cl.$^7$ ........................ G01N 33/53; G01N 33/573; C07D 257/04

[52] U.S. Cl. .............. 435/7.4; 435/7.6; 436/63; 534/652; 548/250; 548/252

[58] Field of Search ............ 435/7.4, 7.6; 436/63; 534/652; 548/252, 250

[56] References Cited

FOREIGN PATENT DOCUMENTS 56-61366  5/1981  Japan .
56-61367  5/1981  Japan .
7-70092   3/1995  Japan .

OTHER PUBLICATIONS

English Language Abstract of JP No. 7–70092. (1995).
English Language Abstract of JP No. 56–61366. (1981).
English Language Abstract of JP No. 56–61367. (1981).
Ishiyama et al., Chem. Pharm. Bull., vol. 41, No. 6, pp. 1118–1122, 1993, "A New Sulfonated Tetrazolium Salt That Produces a Highly Water–Soluble Formazan Dye".
Ishiyama et al., *Talanta* 44 (1997) 1299–1305.
English Language translation of JP 7–70092. (1995).

*Primary Examiner*—Johann Richter
*Assistant Examiner*—Jane C. Oswecki
*Attorney, Agent, or Firm*—Greenblum & Bernstein, P.L.C.

[57] ABSTRACT

Tetrazolium salt compounds represented by the following general formula (1):

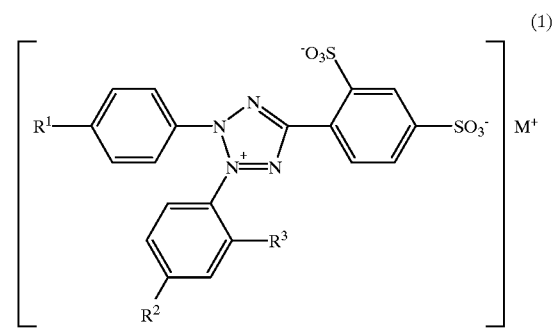

wherein $R^1$ and $R^2$ independently represent hydrogen atom, nitro group, cyano group, carboxyl group or a halogen atom, preferably nitro group; $R^3$ represents an alkyl group or an alkoxyl group, preferably methyl group or methoxy group; and M represents an alkali metal or an ammonium. The compounds are useful for quantitative measurement of a dehydrogenase, and characterized to have high water-solubility and excellent storage stability in the state of an aqueous solution.

14 Claims, 3 Drawing Sheets

WATER-SOLUBLE TETRAZOLIUM SALT COMPOUNDS

This application is a 371 of PCT/JP97/01324 field Apr. 17, 1997.

TECHNICAL FIELD

The present invention relates to novel water-soluble tetrazolium salt compounds. More specifically, the present invention relates to water-soluble tetrazolium salt compounds which can be suitably used for, for example, quantitative measurement of dehydrogenases and other, and to methods for measurement by using the compounds.

BACKGROUND ART

Quantitative measurement of various dehydrogenases, such as lactate dehydrogenase (abbreviated occasionally as "LDH" hereinafter in the specification), alcohol dehydrogenase, and glutamate dehydrogenase, have conventionally been conducted by using tetrazolium salt compounds. A property of the tetrazolium salt compound is its ability to receive a hydrogen released by the action of a dehydrogenase, among variety types as mentioned above, via an intermediate electron transporter such as reduced nicotinamide-adenine dinucleotide (abbreviated occasionally as "NADH" hereinafter in the specification) to give a corresponding formazan compound. Accordingly, dehydrogenases can be quantitatively determined by measuring the absorbance of the resulting formazan compound.

Among these dehydrogenases, lactate dehydrogenase distributes all over somatic cells, and in particular, abundantly exists in myocardia, livers, skeletal muscles, and kidneys. It is known that serum LDH activity markedly increases in patients suffered from diseases such as myocardial infarct, malignant tumor, hepatic failure, progressive muscular atrophy, intravascular hemolysis, and megaloblastic anemia. Accordingly, by measuring serum LDH activity, highly useful clinical information for diagnosis can be obtained.

In recent years, in order to detect trace substances in blood, e.g., uric acid and bile acid, with high sensitivity, it has been desired to develop a method for measuring a dehydrogenase which is less susceptible to biogenous substances. For this purpose, 3,3'-[3,3'-dimethoxy-(1,1'-biphenyl)-4,4'-diyl]-bis[2-(4-nitrophenyl)-5-phenyl]-2H-tetrazolium chloride (abbreviated occasionally as "nitro-TB" hereinafter in the specification) and other have generally been used as hydrogen acceptors.

However, the formazan compound formed by nitro-TB after the acceptance of a hydrogen has low water solubility, which causes a practical problem. In particular, in automatic analysis, the resulting formazan compound precipitates inside a measuring system including tubes and cells, and may add positive errors on measured values. In order to solve the problem, it has been desired to develop a method utilizing a tetrazolium salt which produces a water-soluble formazan compound.

As water-soluble tetrazolium salt compounds which form formazan compounds having sufficient solubility, Japanese Patent Unexamined Publication No.(Hei)7-70092/1995 discloses compounds of the following general formula (2):

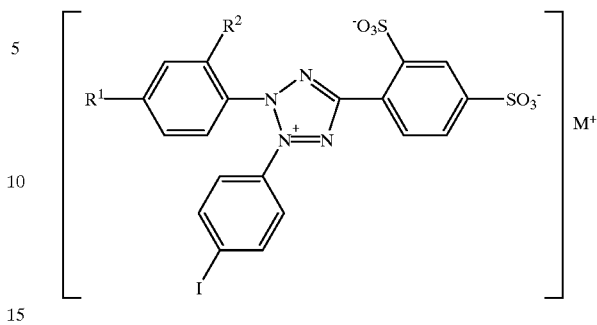

wherein $R^1$ and $R^2$ independently represent hydrogen atom or nitro group, and M represents an alkali metal or an ammonium.

Since these compounds produce formazan compounds having extremely high detection sensitivity, measurement with higher sensitivity can be achieved by using these compound compared to the conventionally used nitro-TB. In addition, because of the water-solubility of the formazan compounds, they are free from adhesion to a measuring apparatus, and accordingly, useful for clinical diagnostics. In particular, the compounds of the above general formula wherein $R^1$ and $R^2$ are nitro groups have a feature of efficient reactivity with NADH to give a formazan compound exhibiting extremely high absorbance.

However, researches by the inventors of the present invention revealed that these compounds have a problem of low storage stability when stored in the state of an aqueous solution. Because aqueous solutions are often stored, after their preparation, for a long period of time such as for 3 to 6 months in usual clinical analyses, it is desired that tetrazolium compounds used as hydrogen acceptors have high storage stability in the state of an aqueous solution.

DISCLOSURE OF THE INVENTION

The inventors of the present invention conducted various studies to provide compounds which have high storage stability as an aqueous solution, and in addition, maintains the characteristic excellent detection sensitivity of the compounds of the general formula (2). As a result, they found that the compounds of the general formula (1) set out below have the desired features. The present invention was achieved on the basis of these findings.

The present invention thus provides tetrazolium salt compounds represented by the following general formula (1):

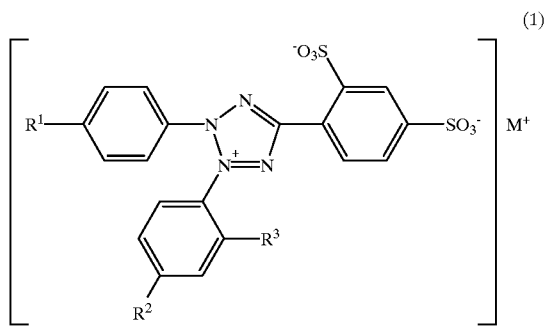

wherein $R^1$ and $R^2$ independently represent hydrogen atom, nitro group, cyano group, carboxyl group, or a halogen atom; $R^3$ represents an alkyl group or an alkoxyl group, and M represents an alkali metal or an ammonium.

According to preferred embodiments of the present invention, there are provided the aforementioned tetrazolium salt compounds wherein both $R^1$ and $R^2$ are nitro groups, and $R^3$ is a $C_{1-4}$ alkyl group or a $C_{1-4}$ alkoxy group, and the aforementioned tetrazolium salt compounds wherein both $R^1$ and $R^2$ are nitro groups, $R^3$ is methyl group or methoxy group, and M is sodium.

According to another aspect of the present invention, there is provided a reagent for the measurement of a dehydrogenase which comprises the aforementioned tetrazolium salt compound. As a preferred embodiment of the present invention, there is provided the aforementioned reagent which is used for a measurement utilizing reduced nicotinamide adenine dinucleotide as an intermediate electron transporter.

According to further aspect of the present invention, there are provided formazan compounds represented by the following general formula (6):

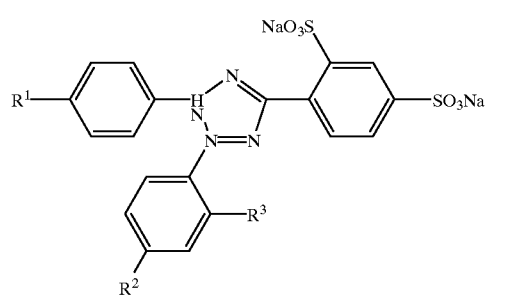

(6)

wherein $R^1$ and $R^2$ independently represent hydrogen atom, nitro group, cyano group, carboxyl group or a halogen atom, and $R^3$ represents an alkyl group or an alkoxyl group.

According to still further aspect of the present invention, there is provided a method for the measurement of a dehydrogenase wherein the compound of the above general formula (1) is used as a hydrogen acceptor. According to preferred embodiments of the aforementioned methods, there are provided the method which comprises the step of measuring the absorbance of the formazan compound represented by the above general formula (6); and the method wherein reduced nicotinamide adenine dinucleotide is used as an intermediate electronic transporter.

BEST MODE FOR CARRYING OUT THE INVENTION

Figure 1:
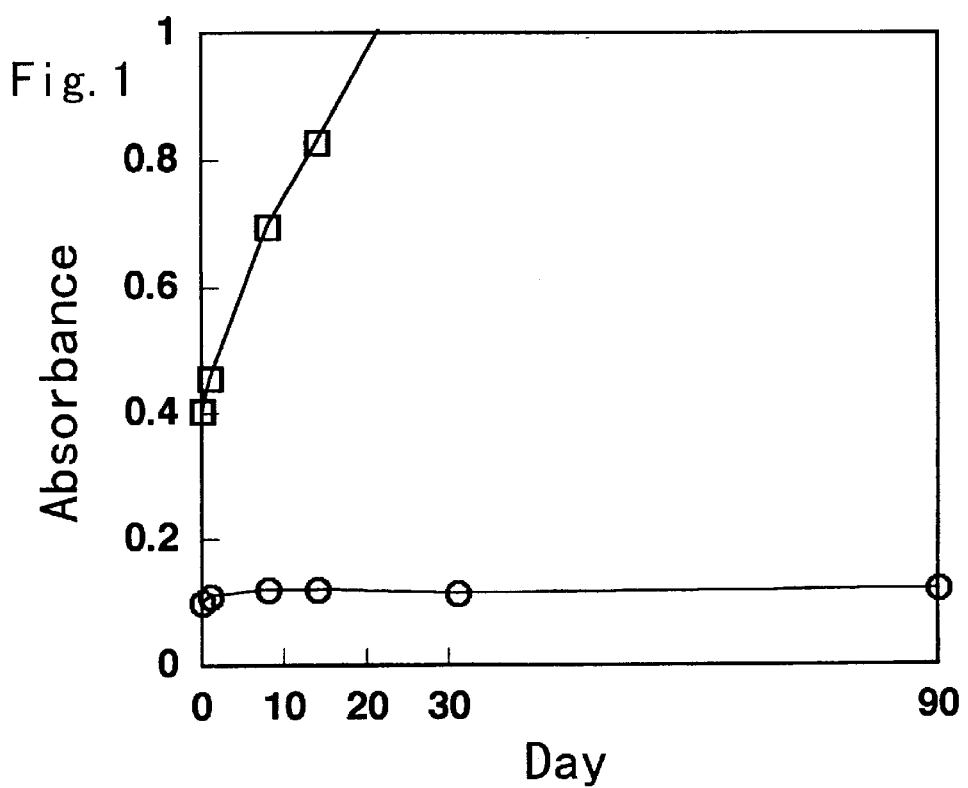
FIG. 1 depicts the changes of absorbance of the compound of the present invention (Compound a) represented by ○ and a compound disclosed in Japanese Patent Unexamined Publication No.(Hei) 7-70092/1995 (Compound b) represented by □ when stored at 4° C.

In the above general formula (1), $R^1$ and $R^2$ independently represent hydrogen atom, nitro group, cyano group, carboxyl group or a halogen atom. As the halogen atom, any of fluorine atom, chlorine atom, bromine atom, and iodine atom can be used. It is preferred that both $R^1$ and $R^2$ nitro groups.

As the alkyl group represented by $R^3$, for example, a $C_{1-4}$ alkyl group can be used. More specifically, methyl group, ethyl group, n-propyl group, isopropyl group, n-butyl group, sec-butyl group, tert-butyl group and other can be used. As the alkoxy group represented by $R^3$, for example, a $C_{1-4}$ alkoxy group can be used. More specifically, methoxy group, ethoxy group, n-propoxy group, isopropoxy group, n-butoxy group, sec-butoxy group, tert-butoxy group and other can be used. $R^3$ may preferably be a $C_{1-4}$ alkyl group or a $C_{1-4}$ alkoxy group, and more preferably methyl group or methoxy group.

As the alkali metal represented by M, for example, sodium, potassium and other can be used, and sodium is preferred.

The compounds of the present invention represented by the general formula (1) can be prepared by a conventional method. For example, a hydrazine compound represented by the following general formula (3):

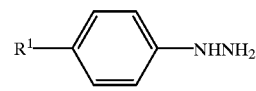

(3)

wherein $R^1$ represents hydrogen atom. nitro group, cyano group carboxyl group or a halogen atom can be reacted with an aldehyde compound represented by the general formula (4):

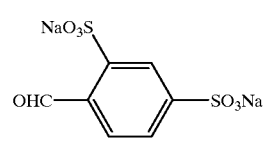

(4)

in an alcoholic solution to obtain a hydrazone compound represented by the general formula (5):

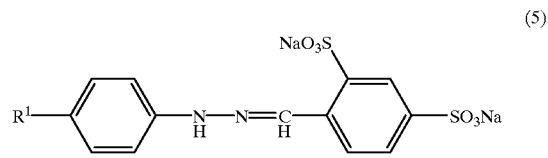

(5)

and then the resulting compound can be reacted with a corresponding diazonium salt in an organic solvent or water under basic condition to obtain a formazan compound represented by the general formula (6).

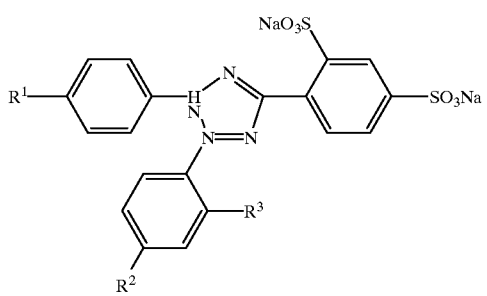

(6)

In the above general formula (6), $R^1$ and $R^2$ independently represent hydrogen atom, nitro group, cyano group, carboxyl group, or a halogen atom, and $R^3$ represents an alkyl group or an alkoxyl group, and they may preferably be the substituents specifically explained as to $R^1$, $R^2$ and $R^3$ of the above general formula (1).

In the reactions mentioned above, sodium hydroxide, potassium hydroxide or other may be used as a basifying agent. Then, the resulting formazan compound of the general formula (6) can be oxidized by using an oxidizing agent such as butyl nitrite in an alcoholic solvent to obtain the tetrazolium salt compound of the general formula (1).

The compounds of the present invention have a characteristic feature that they receive a hydrogen produced by the action of a dehydrogenase via NADH or other, and they, per se, are reduced to form the formazan compounds represented by the above general formula (6). Accordingly, the concentration of a dehydrogenase such as lactate dehydrogenase, alcohol dehydrogenase, and glutamate dehydrogenase can be quantitatively measured by using the compounds of the present invention as hydrogen acceptors. They can also be used for quantitative measurement of reducing substances such as NADH as described in the following examples. In general, the absorbance of the formazan compound of the general formula (6) formed in a reaction system may be measured to perform the quantitative measurement of these substances, or alternatively, the measurement can also be performed by means of fluorescent measurement or other spectrometric means. Methods for the measurement of a dehydrogenase utilizing an intermediate electronic transporter such as NADH are well known in the art, per se, and reaction conditions, measurement means and other can be appropriately chosen by one of ordinary skill in the art.

EXAMPLES

The present invention will be further explained more specifically by referring to the following examples. However, the scope of the present invention is not limited to the following examples.

Example 1

Synthesis of the Compound of the General Formula (1) wherein $R^1$ and $R^2$ are Nitro Groups and $R^3$ is Methoxy Group (Compound a)

p-Nitrophenylhydrazine (18.4 g) and sodium 4-formyl-1,3-benzenedisulfonate (37.2 g) were mixed with methanol, and the mixture was heated under reflux for two hours. The resulting precipitates were collected by filtration to obtain a hydrazone in a 85% yield. The hydrazone obtained (6.7 g) was dissolved in water (200 ml), and cooled to 0° C. Separately, 5-nitro-o-anisidine (2.7 g) was diazotized in a conventional manner, and the product was added to the hydrazone solution obtained above. The reaction mixture was kept at -5 to 0° C. and added dropwise with an aqueous solution obtained by dissolving NaOH (2.6 g) in water (40 ml). After the dropwise addition, the mixture was stirred overnight at room temperature. The reaction mixture was added with hydrochloric acid and concentrated. The precipitates formed by the addition of isopropanol were collected by filtration to obtain a formazan in a 63% yield. The resulting formazan (5 g) was suspended in methanol (250 ml), added with concentrated hydrochloric acid (6.7 ml) and butyl nitrite (4.1 g), and then the mixture was stirred at room temperature overnight. The reaction mixture was concentrated, and added with isopropanol. The deposited precipitates were collected by filtration, and the crude product was recrystallized from ethanol to obtain the captioned tetrazolium salt (Compound a) in a 45% yield.

Elemental analysis: Calculated. ($C_{20}H_{12}N_6O_{11}S_2Na$) C: 40.00%, H: 2.18%, N: 14.00% Found. C: 39.78%, H: 2.15%, N: 13.76%

Example 2

Synthesis of the Compound of the General Formula (1) wherein $R^1$ and $R^2$ are Nitro Groups and $R^3$ is Methyl Group The captioned compound was prepared in the same manner as in Example 1. Elemental analysis: Calculated. ($C_{20}H_{13}N_6O_{10}S_2Na$) C: 41.10% H: 2.24% N: 14.38%; Found. C: 40.86%, H: 2.44%, N: 14.17%

Example 3

Storage stability test 50 mM Tris buffer (pH 8.0) containing 1 mM of Compound a was stored at 4° C. for 0, 1, 7, 14, 31 and 90 days, and absorbances at 460 nm were measured. At the same time, the compound of the above general formula (2) described in Japanese Patent Unexamined Publication No. (Hei) 7-70092/1995 wherein both $R^1$ and $R^2$ are nitro groups (Compound b: see, the section of "Background Art") was stored in the same manner, and changes of absorbance were measured. FIG. 1 shows the relationships between the days of storage and absorbances deriving from Compound a and Compound b. Compound b exhibited remarkable increases of absorbance, whilst Compound a of the present invention gave no increase of absorbance for 90 days, which revealed its excellent stability.

Example 4

Figure 2:
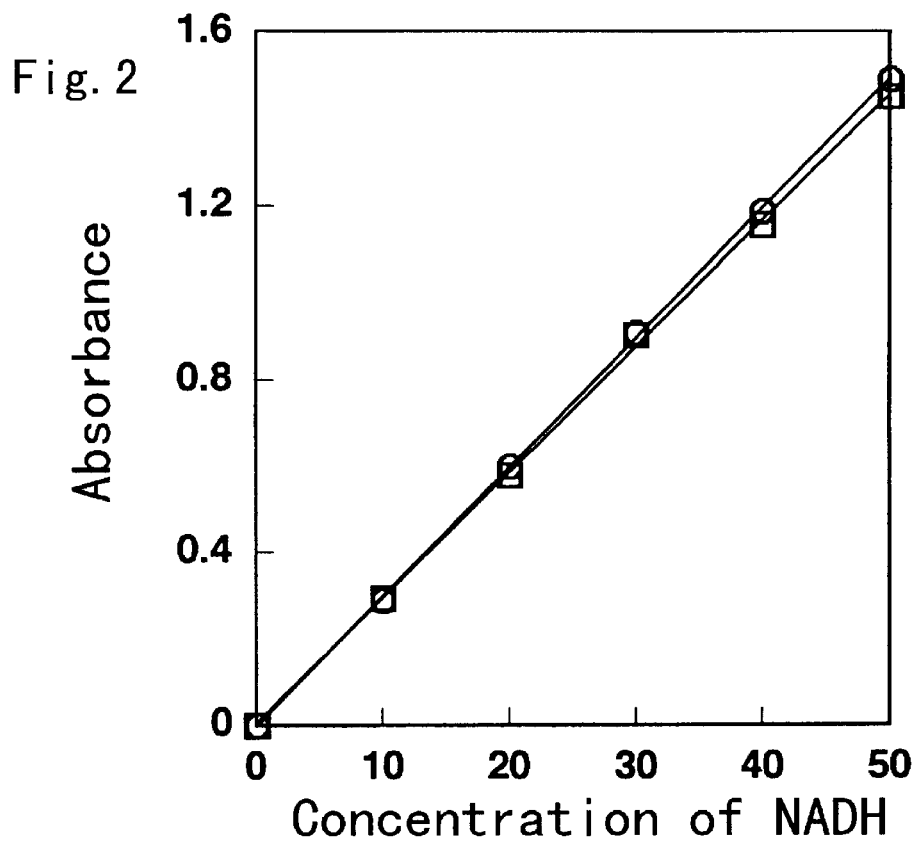
FIG. 2 depicts calibration curves of NADH obtained by absorption spectrum measurements. In the figure, ○ represents results obtained by using the compound of the present invention (Compound a), and □ represents results obtained by using the compound disclosed in Japanese Patent Unexamined Publication No.(Hei) 7-70092/1995 (Compound b).
Figure 3:
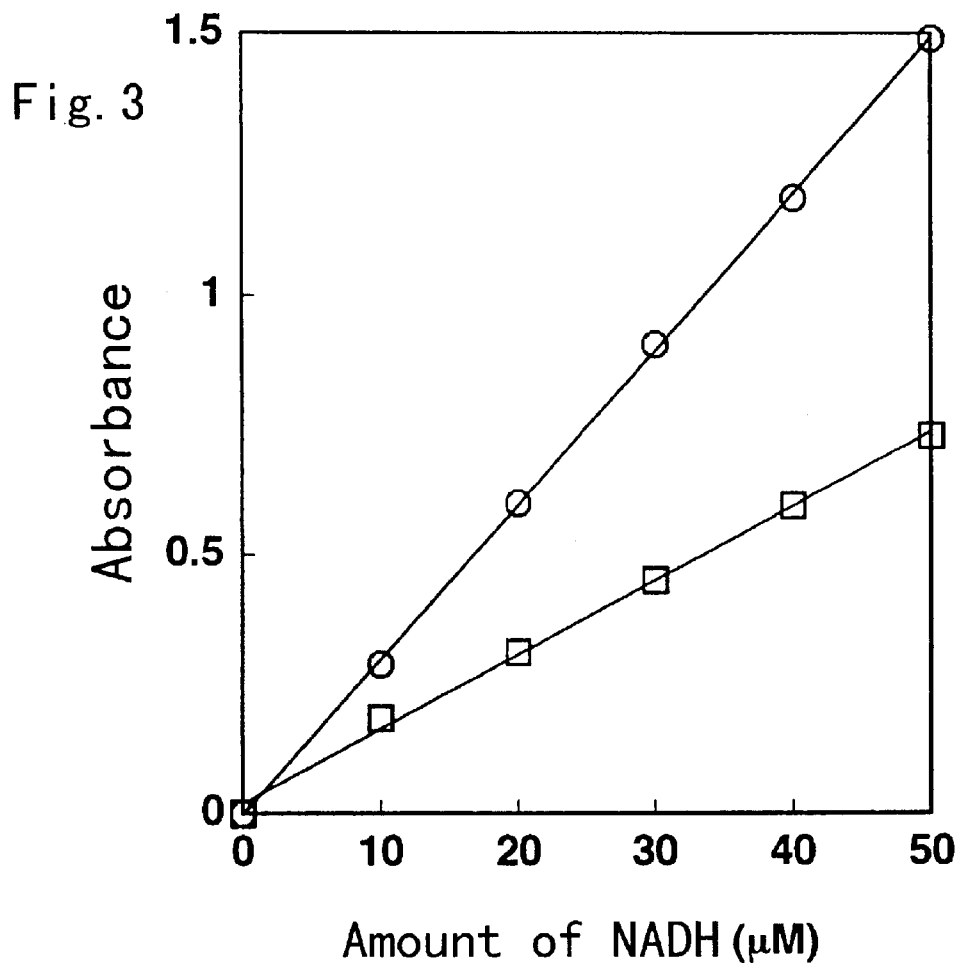
FIG. 3 depicts calibration curves of NADH obtained by absorption spectrum measurements. In the figure, ○ represents results obtained by using the compound of the present invention (Compound a), and □ represents results obtained by using nitro-TB.

Measurement of NADH Concentration 50 mM Tris buffer (pH 8.0, 5 ml) containing 0.1 mM. of Compound a and 5μ M of 1-methoxy-5-methylphenazinium methosulfate was added with 0, 10, 20, 30, 40 or 50 μl of 5 mM NADH, and allowed to react at room temperature for 5 minutes, and then absorbances were measured. FIG. 2 shows the relationship between NADH concentrations and absorbances. Measurement was performed in the same manner by using Compound b. Each of the compounds gave a linear calibration curve between NADH concentration and absorbance starting from the origin, and exhibited almost the same detection sensitivity. On the other hand, when the relationship between NADH concentration and absorbance was measured by using nitro-TB in the same manner, it was found that detection sensitivity was apparently inferior to that of the compound of the present invention as shown in FIG. 3.

INDUSTRIAL APPLICABILITY

The tetrazolium salt compounds of the present invention give water-soluble formazans when used as hydrogen acceptors. Accordingly, no deposition is occurred in a measuring apparatus, and measurements by using automatic analyzers are facilitated. Furthermore, the compounds of the present invention have characteristics that they exhibit higher sensitivity compared to nitro-TB, which is generally used as a hydrogen acceptor in clinical diagnostics, and can easily detect NADH. In addition, they have the feature of excellent storage stability in the state of an aqueous solution. Accordingly, the compounds of the present invention are extremely useful as, for example, reagents for clinical diagnostics.

What is claimed is:

1. tetrazolium salt compound represented by the following general formula (1):

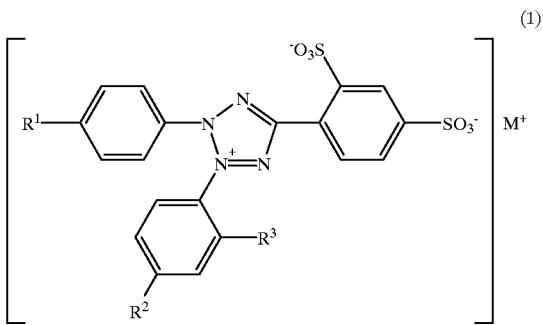

(1)

wherein $R^1$ and $R^2$ independently represent hydrogen atom, nitro group, cyano group, carboxyl group, or a halogen atom; $R^3$ represents an alkyl group or an alkoxyl group, and M represents an alkali metal or an ammonium.

2. The tetrazolium salt compound according to claim 1 wherein both $R^1$ and $R^2$ are nitro groups; and $R^3$ is a $C_{1-4}$ alkyl group or a $C_{1-4}$ alkoxy group.

3. The tetrazolium salt compound according to claim 1 wherein both $R^1$ and $R^2$ are nitro groups; $R^3$ is methyl group or methoxy group; and M is sodium.

4. A reagent for the measurement of a dehydrogenase which comprises a compound according to claim 1.

5. The reagent according to claim 4 which is used for a measuring process utilizing reduced nicotinamide adenine dinucleotide as an intermediate electron transporter.

6. A formazan compound represented by the following general formula (6):

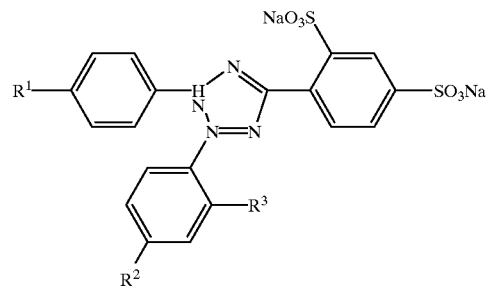

(6)

wherein $R^1$ and $R^2$ independently represent hydrogen atom, nitro group, cyano group, carboxyl group, or a halogen atom; and $R^3$ represents an alkyl group or an alkoxyl group.

7. A method for the measurement of a dehydrogenase wherein a compound according to claim 1 is used as a hydrogen acceptor.

8. The method according to claim 7 which comprises the step of measuring the absorbance of a formazan compound according to claim 6.

9. The method according to claim 7 wherein reduced nicotinamide adenine dinucleotide is used as an intermediate electronic transporter.

10. A reagent for the measurement of a dehydrogenase which comprises a compound according to claim 2.

11. A reagent for the measurement of a dehydrogenase which comprises a compound according to claim 3.

12. A method for the measurement of a dehydrogenase wherein a compound according to claim 2 is used as a hydrogen acceptor.

13. A method for the measurement of a dehydrogenase wherein a compound according to claim 3 is used as a hydrogen acceptor.

14. The method according to claim 8 wherein reduced nicotinamide adenine dinucleotide is used as an intermediate electronic transporter.

* * * * *